(12) United States Patent
Dagle et al.

(10) Patent No.: US 9,663,435 B1
(45) Date of Patent: May 30, 2017

(54) PROCESS FOR CONVERSION OF LEVULINIC ACID TO KETONES

(71) Applicant: BATTELLE MEMORIAL INSTITUTE, Richland, WA (US)

(72) Inventors: Vanessa M. Dagle, Richland, WA (US); Robert A. Dagle, Richland, WA (US)

(73) Assignee: BATTELLE MEMORIAL INSTITUTE, Richland, WA (US)

( * ) Notice: Subject to any disclaimer, the term of this patent is extended or adjusted under 35 U.S.C. 154(b) by 0 days.

(21) Appl. No.: 15/189,808

(22) Filed: Jun. 22, 2016

(51) Int. Cl.
| | |
|---|---|
| *C07C 45/54* | (2006.01) |
| *C07C 1/207* | (2006.01) |
| *C10L 1/04* | (2006.01) |
| *B01J 23/72* | (2006.01) |
| *B01J 23/06* | (2006.01) |
| *B01J 37/02* | (2006.01) |
| *B01J 37/08* | (2006.01) |

(52) U.S. Cl.
CPC .............. *C07C 45/54* (2013.01); *B01J 23/06* (2013.01); *B01J 23/72* (2013.01); *B01J 37/0201* (2013.01); *B01J 37/0236* (2013.01); *B01J 37/08* (2013.01); *C07C 1/2078* (2013.01); *C10L 1/04* (2013.01); *C07C 2101/14* (2013.01); *C07C 2523/06* (2013.01); *C10L 2200/0469* (2013.01)

(58) Field of Classification Search
CPC ........ C07C 45/54; C07C 45/57; C07C 1/2078
See application file for complete search history.

(56) References Cited

U.S. PATENT DOCUMENTS

| | | | |
|---|---|---|---|
| 7,960,592 | B1 | 6/2011 | Dumesic et al. |
| 2014/0171688 | A1 | 6/2014 | Karanjikar et al. |

OTHER PUBLICATIONS

Bond, J. Q., et al., Integrated Catalytic Conversion of y-Valerolactone to Liquid Alkenes for Transportation Fuels, Science, 327, 2010, 1110-1115.
Bond, J. Q., et al., Production of renewable jet fuel range alkanes and commodity chemicals from integrated catalytic processing of biomass, Energy & Environmental Science, 7, 2014, 1500-1523.
Dagle, R. A., et al., Cutting-edge research for a greener sustainable future, Green Chemistry, 18, 7, 2016, 1821-2242.
Gong, Y., et al., Oxidative Decarboxylation of Levulinic Acid for Cupric Oxides, Molecules, 15, 2010, 7946-7960.
Gong, Y., et al., Oxidative Decarboxylation of Levulinic Acid by Silver(I)/Persulfate, Molecules, 16, 2011, 2714-2725.
Smith, C., et al., Conversion of syngas-derived C2+ mixed oxygenates to C3-C5 olefins over ZnxZryOz mixed oxide catalysts, Catalysis Science & Technology, DOI: 10.1039/c5cy01261a, 2105, 1-121.

*Primary Examiner* — Sikarl Witherspoon
(74) *Attorney, Agent, or Firm* — James D. Matheson

(57) ABSTRACT

A method for generating desired platform chemicals from feedstocks such as cellulosic biomass feedstocks containing levulinic acid by decarboxylating a feed stock comprising levulinic acid to generate ketones. This is done by passing a feed stock comprising levulinic acid in a gas phase over a non-precious metal catalyst on a neutral support.

19 Claims, 1 Drawing Sheet

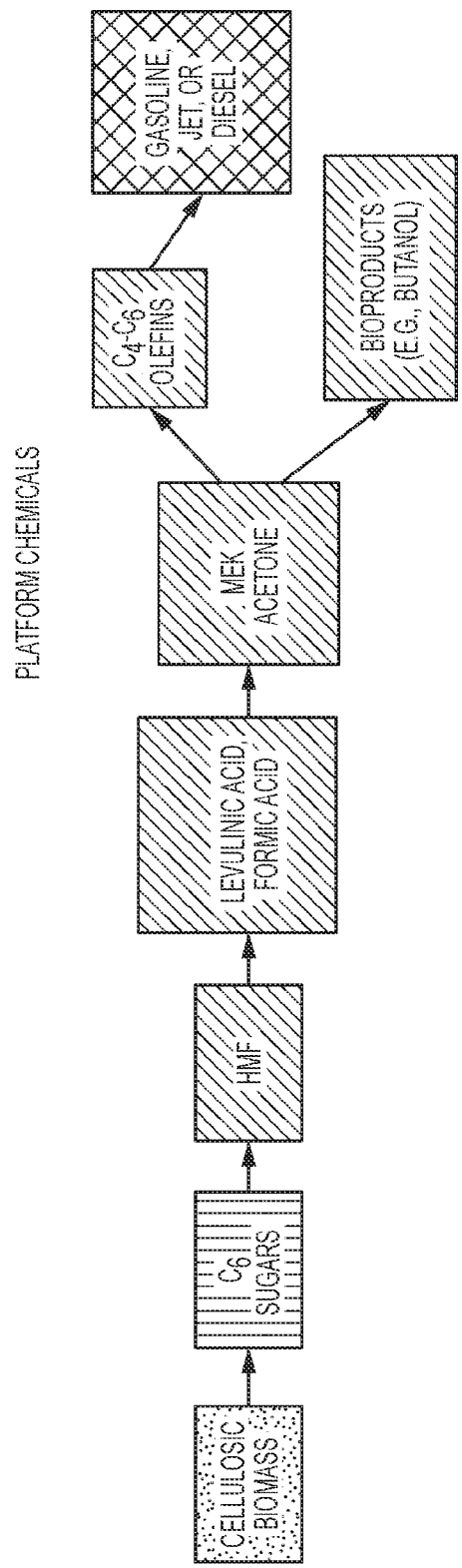

PROCESS FOR CONVERSION OF LEVULINIC ACID TO KETONES

STATEMENT REGARDING RIGHTS TO INVENTION MADE UNDER FEDERALLY-SPONSORED RESEARCH AND DEVELOPMENT

This invention was made with Government support under Contract DE-AC05-76RL01830 awarded by the U.S. Department of Energy. The Government has certain rights in the invention.

FIELD OF THE INVENTION

The present invention relates generally to processes for converting cellulosic biomass feedstocks into bio-renewable hydrocarbon fuels. More particularly, the invention relates to conversion of levulinic acid to ketones suitable for use as commodity chemicals or as feedstocks for conversion into bio-products and hydrocarbon fuels.

BACKGROUND OF THE INVENTION

Levulinic acid (LA) ($C_5H_8O_3$) (MW=116.115) is a top building block obtained from biomass-derived sugars. Advances in conversion of cellulose-derived biomass to date have resulted in selective yields of levulinic acid (LA) of up to about 80% at a production cost of about 5 cents (U.S.) per pound. Consequently, significant R&D efforts have now been extended to develop chemicals and fuels that originate from LA. LA-derived chemicals find application in the chemical industry as solvents and plasticizers, in the food industry and in other applications. However, current methods for upgrading biomass-derived sugars including hexoses (6-carbon sugars) and pentoses (5-carbon sugars) are limited by a lack of robust catalysts, high operating costs, and low yields. For example, y-valerolactone (GVL) ($C_5H_8O_2$) (MW=110.116) is one potential intermediate in the production of transportation fuels. GVL may be produced from LA, which in turn can be derived from biomass-derived hexoses. However, a major drawback of this process is the need for precious metal catalysts to effect hydrogenation that impart a high cost for conversion of each unit of LA to GVL. Further, yields of chemicals stemming from dehydration of GVL such as methyl ethyl ketone (MEK) and acetone are small. The insignificant yields of these platform chemicals renders this process economically unsuitable for production of either the commodity chemicals or subsequent conversion into transportation fuels. Furthermore, the formation of cyclic intermediates can lead to formation of coke deposits during reaction that can rapidly deactivate necessary catalysts. Current upgrading methods for sugars are limited by a lack of catalyst robustness, high operating costs, and low yield.

Accordingly, new and efficient catalytic processes are needed that convert LA to selected conversion products including commodity chemicals such as MEK and acetone at appreciable yields suitable for use in bio-refineries for conversion into liquid transportation fuels. The present invention addresses these needs.

SUMMARY OF THE INVENTION

The present invention is a method for generating desired platform chemicals from feedstocks such as cellulosic biomass feedstocks containing levulinic acid by decarboxylating a feed stock comprising levulinic acid to generate ketones. This is done by passing a feed stock comprising levulinic acid in a gas phase over a non-precious metal catalyst on a neutral support at a temperature between 250-650 degrees C. In one instantiation the gas-phase feedstock over a non-precious metal catalyst occurs without the presence of a reducing gas. Preferably, the feedstock is introduced continuously over the decarboxylation catalyst to continuously form ketones. In various embodiments the catalyst may be a transition metal catalyst, and preferably a transition metal selected from the metals in group VIII, group IX, group X, or group XI on the periodic table. Preferably the catalyst is Cu on a neutral carbon support. For purposes of this application the term neutral refers to a pH in the range between 5.5 and 8.

A neutral support is preferably a carbon material (activated carbon, carbon black and graphite, carbon fiber, carbon nanotubes), more preferably an activated carbon support made from almond core, coconut shell, palm tree wood or coal, preferably coconut shell. In other embodiments neutral supports include oxides such as $SiO_2$, $Al_2O_3$, $ZrO_2$, $TiO_2$, $Ta_2O_5$, $CeO_2$, MgO, $La_2O_3$, $Nb_2O_5$, and combinations thereof. In some instances these materials are modified with at least one alkali and/or alkaline earth metals, and/or group III metals (e.g. Li, Na, K, Rb, Cs, Be, Mg, Ca, Sr, Ba, Y).

In some instances a method for generating fuels is described wherein fuels are formed from a biomass feedstock by decarboxylating the levulinic acid in the feedstock by passing the feed stock over a metal catalyst on a neutral support at a temperature between 250-650 degrees C. to generate ketone products and then converting the ketone products over an olefin-forming catalyst to form an olefin. In some embodiments the olefin-forming catalyst is an acid base catalyst. In some applications the passing of the gas-phase feedstock over a metal catalyst occurs without the presence of a reducing gas. In various embodiments the metal catalyst may be a transition metal catalyst, and preferably a transition metal selected from the metals in group VIII, group IX, group X, or group XI on the periodic table. The methods of the present invention can utilize non-precious metals to effectuate the results thus providing a cost savings over the prior art. In one arrangement the catalyst is Cu on a neutral carbon support.

A neutral support is preferably a carbon material (activated carbon, carbon black and graphite, carbon fiber, carbon nanotubes), more preferably an activated carbon support made from almond core, coconut shell, palm tree wood or coal, preferably coconut shell. In other embodiments neutral supports include oxides such as $SiO_2$, $Al_2O_3$, $ZrO_2$, $TiO_2$, $Ta_2O_5$, $CeO_2$, MgO, $La_2O_3$, $Nb_2O_5$, and combinations thereof. In some instances these materials are modified with at least one alkali and/or alkaline earth metals, and/or group III metals (e.g. Li, Na, K, Rb, Cs, Be, Mg, Ca, Sr, Ba, Y). In some embodiments the olefin-forming catalyst has a formula of $Zn_xZr_yO_z$ where x is selected from 0.5 to 15, y is selected from 0.5 to 20, and z is selected from 0.5 to 55. Continuous feeding of the feedstock through the process allows for conversion of levulinic acid from cellulosic biomass to ketone based chemical and further upgrading of those chemicals into to other platform and commodity chemicals as well as desirable fuels (jet/diesel) at a scale relevant for industrial biomass implementation.

The purpose of the foregoing abstract is to enable the United States Patent and Trademark Office and the public generally, especially the scientists, engineers, and practitioners in the art who are not familiar with patent or legal terms or phraseology, to determine the nature and essence of the technical disclosure of the application. The abstract is neither intended to define the invention of the application, which is measured by the claims, nor is it intended to be limiting as to the scope of the invention in any way.

BRIEF DESCRIPTION OF THE DRAWINGS

FIG. 1 shows a process for conversion of biomass containing levulinic acid and formic acid derived from cellulose-containing biomass feedstocks into platform chemicals, and fuels according to one embodiment of the present invention.

DETAILED DESCRIPTION

In the following description, embodiments of the present invention are shown and described by way of illustration of the best mode contemplated for carrying out the invention. It will be clear that the invention may include various modifications and alternative constructions. Accordingly, the description of the preferred embodiments should be seen as illustrative only and not limiting. The present invention includes all modifications, alternative constructions, and equivalents falling within the spirit and scope of the invention as defined in the claims.

FIG. 1 shows a block flow diagram of an exemplary process for converting biomass to fuels through a process whereby levulinic acid (LA) is converted to ketone intermediates including, for example, methyl ethyl ketone (MEK) and acetone, which are then utilized individually as specialty, intermediate or commodity chemicals or which can be further upgraded as turned into carbon chain fuels or other chemicals. The focal point of this process is outlined as the step wherein a catalytic process for the conversion of sugar-derived levulinic acid to fuels and chemicals, via platform intermediates MEK and acetone is performed using inexpensive (non-precious metal) catalysts. This then enables a one-step conversion of MEK and acetone to olefin fuel precursors. Currently obtained from petroleum, the annual worldwide production of MEK and acetone is approximately 2 and 6 million tons/yr, respectively, with market selling prices of 74 and 64¢/lb, respectively.

The direct decarboxylation of LA provides the simplest pathway, to a singular product (MEK) and whereby the formation of cyclic intermediates does not occur, nor is H2 required. Cyclic intermediates can lead to the formation of lactones that polymerize and deactivate catalysts through coke deposits. While a dehydration and/or hydrogenation process is typically utilized, preliminary results recently obtained at PNNL indicate careful control of operating parameters and choice of catalyst can actually favor the decarboxylation pathway and increase the yields of MEK, acetone, and without addition of external H2. These results were obtained with non-precious metal catalysts and at atmospheric pressure. This is done by passing a feed stock comprising levulinic acid in a gas phase over the metal catalyst on a neutral support at a temperature between 250-650 degrees C. In one instantiation the gas-phase feedstock over a metal catalyst occurs without the presence of a reducing gas. Preferably, the feedstock is introduced continuously over the decarboxylation catalyst to continuously form ketones. In various embodiments the catalyst may be a transition metal catalyst, and preferably a transition metal selected from the metals in group VIII, group IX, group X, or group XI on the periodic table. Preferably the catalyst is copper (Cu) on a neutral carbon support.

The neutral support is preferably a carbon material (activated carbon, carbon black and graphite, carbon fiber, carbon nanotubes), more preferably an activated carbon support made from almond core, coconut shell, palm tree wood or coal, preferably coconut shell. In other embodiments neutral supports include oxides such as $SiO_2$, $Al_2O_3$, $ZrO_2$, $TiO_2$, $Ta_2O_5$, $CeO_2$, MgO, $La_2O_3$, $Nb_2O_5$, and combinations thereof. In some instances these materials are modified with at least one alkali and/or alkaline earth metals, and/or group III metals (e.g. Li, Na, K, Rb, Cs, Be, Mg, Ca, Sr, Ba, Y). Once the ketones, typically MEK and acetone, are created they can be passed on to a second step for processing and fuel creation and chemical upgrading through an olefin forming process.

The MEK, acetone and other ketones that are created from this arrangement can be then converted into olefin fuel precursors through a simple one step process. In some embodiments the olefin-forming process includes passing the material over a olefin forming catalyst having a formula of $Zn_xZr_yO_z$ where x is selected from 0.5 to 15, y is selected from 0.5 to 20, and z is selected from 0.5 to 2. Continuous feeding of the feedstock through the process allows for conversion of Levulinic acid from cellulosic biomass to ketone based chemicals and further upgrading of those ketone based chemicals into to other platform and commodity chemicals as well as desirable fuels (jet/diesel/gasoline) at a scale relevant for industrial biomass implementation.

In one set of experiments the process was performed with a catalyst on a carbon support that was loaded into a fixed bed reactor between 2 layers of quartz wool. A thermocouple is located in the middle of the bed. The reactor temperature is then increased to 500° C. under nitrogen with a ramp of 3° C./min and held at temperature for 8 hours. The nitrogen flowrate was then adjusted depending of the reaction conditions, the liquid feed pump started and an aqueous solution of levulinic acid is sent through a vaporizer and over the catalyst. Process conditions were operated as follows: W/F (g·s·ml-1) range: between 0.01-20.0, preferentially between 0.1-10.0, more preferentially between 0.3-6.6; Temperature: 250-600° C., preferentially 450-550° C., more preferentially 500° C. Pressure: 1 bar-150 bar, preferentially 1-30 bar, more preferentially 1 bar. While in this instance the reactor was a fixed bed reactor other types of reactors such as fluidized bed reactors, swing reactors, batch reactors or other types of reactors could be utilized. If necessary a nitrogen diluent or other possible diluents such as helium and argon could be utilized. In some applications the reaction could be conducted in absence of diluent. In some applications the levulinic acid (LA) feed can be diluted (preferably with water) to a 5-50 wt % levulinic acid in water, but more preferentially this dilution is between 10-30 wt %, and more preferentially at or about 10 wt %. Formic acid could also be present in the feed without negatively impacting the performance of the process.

The preferred catalysts utilized included at least one metal from the group 8, 9 10, or 11 metal (e.g. Cu, Ag, Pd), preferably Cu supported on a neutral support. The neutral support is preferably a carbon material (activated carbon, carbon black and graphite, carbon fiber, carbon nanotubes), more preferably an activated carbon support made from almond core, coconut shell, palm tree wood or coal, preferably coconut shell. Other neutral supports that could be used are oxides such as $SiO_2$, $Al_2O_3$, $ZrO_2$, $TiO_2$, $Ta_2O_5$, $CeO_2$, MgO, $La_2O_3$, $Nb_2O_5$, and combinations of two or more thereof, modified with at least one alkali and/or alkaline-earth metals and/or group 3 metal (e.g. Li, Na, K, Rb, Cs, Be, Mg, Ca, Sr, Ba, Y). The metal loading is between 0.5-40 wt %, preferentially 1-20 wt %, more preferentially 1-5 wt %. If the neutral support is not a carbon the catalyst can be calcined.

The preferred Cu/activated carbon (coconut shell) catalyst is prepared by incipient wetness impregnation of a Cu metal nitrate precursor dissolved in water onto carbon support, dry at 120° C. for 12 hours and finally calcined at 375° C. under inert gas for 4 hours (i.e. Argon, Nitrogen, Helium). While these preparation steps were utilized the preparation process could vary in numerous ways in order to dispose one or more active metals on the support. Impregnation, ion-exchange incipient wetness impregnation, and/or by drying impregnation as well as other methods in single or multiple step arrangements could all be utilized to combine the catalyst and the support. Likewise, while water and alcohols are used as solvents there is no restriction or limitation upon the particular solvent utilized or the nature of the metal precursor.

The following examples show embodiments of the present disclosure and the experimental results obtained there with. The descriptions of the examples are provided in the following paragraphs and the comparative results are included in Table 1.

Example 1

A 3 wt % Cu/Activated carbon catalyst was prepared by incipient wetness impregnation of an aqueous solution of Cu nitrate. The catalyst was dried at 120° C. for 12 hours then calcined at 375° C. under nitrogen for 4 hours. 2 grams of catalyst sieved 60-100 mesh were loaded in the fixed bed reactor. Before reaction, the catalyst was pretreated under nitrogen at 500° C. for 8 hours. A feed of 10 wt % Levulinic acid (LA) in water, nitrogen diluent with flowing rate equal to 40 sccm, at 500° C., 1 bar and W/F=1.5 g·s·ml-1. In this example 98% of the LA was converted with 33.3% becoming methyl-ethyl ketone (MEK), 16.2% becoming acetone, 8.8% becoming $C_2$-$C_5$ olefins, 20.5% converted to carbon dioxide $CO_2$, 5.5% becoming methane ($CH_4$), 12.8% becoming carbon monoxide (CO), 0.8% becoming $C_2$-$C_5$ paraffins, and 2.1% becoming other oxygenates, such as phenol, cresol, methylcyclopentanone.

Example 2

A 3 wt % Cu/Activated carbon catalyst was prepared by incipient wetness impregnation of an aqueous solution of Cu nitrate. The catalyst was dried at 120° C. for 12 hours then calcined at 375° C. under nitrogen for 4 hours. 2 grams of catalyst sieved 60-100 mesh were loaded in the fixed bed reactor. Before reaction, the catalyst was pretreated under nitrogen at 500° C. for 8 hours. Reactivity measurement was conducted with 10 wt % levulinic acid in water, nitrogen diluent with flowing rate equal to 40 sccm, at 500° C., 1 bar and W/F=3.1 g·s·ml-1. In this example 99.5% of the LA was converted with 36.1% becoming methyl-ethyl ketone (MEK), 5.4% becoming acetone, 8.2% becoming $C_2$-$C_5$ olefins, 29.1% converted to carbon dioxide ($CO_2$), 6.8% becoming methane ($CH_4$), 10.3% becoming carbon monoxide (CO), 1.9% becoming $C_2$-$C_5$ paraffins, and 2.3% becoming other oxygenates.

Example 3

A 3 wt % Cu/Activated carbon catalyst was prepared by incipient wetness impregnation of an aqueous solution of copper (Cu) nitrate. The catalyst was dried at 120° C. for 12 hours then calcined at 375° C. under nitrogen for 4 hours. 2 grams of catalyst sieved 60-100 mesh were loaded in the fixed bed reactor. Before reaction, the catalyst was pretreated under nitrogen at 500° C. for 8 hours. Reactivity measurement was conducted with 10 wt % Levulinic acid in water, nitrogen diluent with flowing rate equal to 40 sccm, at 500° C., 1 bar and W/F=6.3 g·s·ml-1 In this example 99.5% of the LA was converted with 34.6% becoming methyl-ethyl ketone (MEK), 7.2% becoming acetone, 8.1% becoming $C_2$-$C_5$ olefins, 34.6% converted to carbon dioxide $CO_2$, 8.8% becoming methane ($CH_4$), 3.4% becoming carbon monoxide (CO), 2.1% becoming $C_2$-$C_5$ paraffins, and 1.2% becoming other oxygenates Example 4

A 3 wt % Cu/Activated carbon was prepared by incipient wetness impregnation of an aqueous solution of Cu nitrate. The catalyst was dried at 120° C. for 12 hours then calcined at 375° C. under Nitrogen for 4 hours. 2 grams of catalyst sieved 60-100 mesh were loaded in the fixed bed reactor. Before reaction, the catalyst was pretreated under nitrogen at 500° C. for 8 hours. Reactivity measurement was conducted with 10 wt % Levulinic acid in water, nitrogen diluent with flowing rate equal to 40 sccm, at 450° C., 1 bar and W/F=0.8 g·s·ml-1. In this example 99% of the LA was converted with 12.3% becoming methyl-ethyl ketone (MEK), 3.5% becoming acetone, 7.7% becoming $C_2$-$C_5$ olefins, 26.5% converted to carbon dioxide $CO_2$, 5.1% becoming methane ($CH_4$), 19.6% becoming carbon monoxide (CO), 1.7% becoming $C_2$-$C_5$ paraffins, and 9.4% becoming other oxygenates. This example also resulted in the formation of coke within the reactor system.

Example 5

A 3 wt % Cu/Activated carbon was prepared by incipient wetness impregnation of an aqueous solution of Cu nitrate. The catalyst was dried at 120° C. for 12 hours then calcined at 375° C. under Nitrogen for 4 hours. 2 grams of catalyst sieved 60-100 mesh were loaded in the fixed bed reactor. Before reaction, the catalyst was pretreated under nitrogen at 500° C. for 8 hours. Reactivity measurement was conducted with 10 wt % Levulinic acid in water, nitrogen diluent with flowing rate equal to 40 sccm, at 550° C., 1 bar and W/F=1.5 g·s·ml-1. In this example 97% of the LA was converted with 16.5% becoming methyl-ethyl ketone (MEK), 9.3% becoming acetone, 11.1% becoming $C_2$-$C_5$ olefins, 36.0% converted to carbon dioxide $CO_2$, 9.9% becoming methane ($CH_4$), 9.9% becoming carbon monoxide (CO), 2.9% becoming $C_2$-$C_5$ paraffins, and 4.3% becoming other oxygenates. A comparison of these experiments is shown in Table 1.

TABLE 1

| Sample | (%) Converted | Selectivity (%) | | | | | | |
|---|---|---|---|---|---|---|---|---|
| | | MEK | Acetone | $C_2$-$C_5$ olefins | $CO_2$ | $CH_4$ | CO | $C_2$-$C_5$ paraffin | Other oxygenates |
| 1 | 98 | 33.3 | 16.2 | 8.8 | 20.5 | 5.5 | 12.8 | 0.8 | 2.1 |
| 2 | 99.5 | 36.1 | 5.4 | 8.2 | 29.1 | 6.8 | 10.3 | 1.9 | 2.3 |
| 3 | 99.5 | 34.6 | 7.2 | 8.1 | 34.6 | 8.8 | 3.4 | 2.1 | 1.2 |

TABLE 1-continued

| | | | | Selectivity (%) | | | | | |
|---|---|---|---|---|---|---|---|---|---|
| Sample | (%) Converted | MEK | Acetone | $C_2$-$C_5$ olefins | $CO_2$ | $CH_4$ | CO | $C_2$-$C_5$ paraffin | Other oxygenates |
| 4 | 99 | 12.3 | 3.5 | 7.7 | 26.2 | 5.1 | 19.6 | 1.7 | 9.4 |
| 5 | 97 | 16.5 | 9.3 | 11.1 | 36.0 | 9.9 | 9.9 | 2.9 | 4.3 |

The MEK and acetone by products obtained from decarboxylation of levulinic acid can be further converted into olefins over a Zn1Zr2.5Oz catalyst. In one example, Example 6, a Zn1Zr2.5Oz catalyst was prepared via wet impregnation of a Zn(NO3)26H2O solution on Zr(OH)4. The Zr(OH)4 was initially dried overnight at 105° C. to remove any excess water on the surface before impregnation. After impregnation, the catalysts were dried overnight at room temperature and then for 4 hours at 105° C. prior to calcination. The catalyst then was calcined via a 3° C./min ramp to 400° C. for 2 hours, followed by a 5° C./min ramp to the final calcination temperature of 550° C. for 3 hours. 1 gram of catalyst sieved to a 60 100 mesh was loaded in the fixed bed reactor of FIG. 1. Before reaction, the catalyst was pretreated under nitrogen at 450° C. for 8 hours. A feed of 30 wt % MEK in water, a nitrogen/hydrogen (ratio 4:1 molar) mixture diluent with a flow rate equal to 40 sccm, at 450° C., 1 bar and W/F=0.8 g·s·ml-1 was then passed over the catalyst. In this example 89% of the MEK was converted with 50.2% into pentenes, 13.5% into butenes, 2.2% into propylenes, 0.8% into ethylene, 3.8% into methane, 17.1% into CO2, 0.7% into C2-C5 paraffins, 9.1% into acetone and 2.6% into other oxygenates (principally pentanone).

In another example, example 7, a Zn1Zr2.5Ox catalyst was prepared via wet impregnation of a Zn(NO3)26H2O solution on Zr(OH)4. The Zr(OH)4 was initially dried overnight at 105° C. to remove any excess water on the surface before impregnation. After impregnation, the catalysts were dried overnight at room temperature and then for 4 hours at 105° C. prior to calcination. The catalyst then was calcined via a 3° C./min ramp to 400° C. for 2 hours, followed by a 5° C./min ramp to the final calcination temperature of 550° C. for 3 hours. 1 gram of catalyst sieved 60-100 mesh was loaded in the fixed bed reactor. The reactor of FIG. 1 was used. Before reaction, the catalyst was pretreated under nitrogen at 450° C. for 8 hours. Reactivity measurement was conducted with 30 wt % acetone in water, a nitrogen/hydrogen (ratio 4:1 molar) mixture diluent with flowing rate equal to 40 sccm, at 450° C., 1 bar and W/F=0.8 g·s·ml-1. In this example 95% of the acetone was converted with 0.0 converted % into pentenes, 76.5% into butenes, 5.4% into propylenes, 0.0% into ethylene, 5.0% into methane, 12.3% into CO2, 0.0% into C2-C5 paraffins, 0.0% into acetone and 0.8% into other oxygenates (principally acetic acid).

While exemplary embodiments of the present invention have been shown and described, it will be apparent to those skilled in the art that many changes and modifications may be made without departing from the invention in its true scope and broader aspects. The appended claims are therefore intended to cover all such changes and modifications as fall within the scope of the present invention.

What is claimed is:

1. A method for decarboxylating a feed stock comprising levulinic acid to generate ketones comprising the step of: passing a feed stock comprising levulinic acid in a gas phase over a metal catalyst on a neutral support having a pH between 5.5 and 8 at a temperature between 350-650 degrees C.

2. The method of claim 1, wherein the step of passing the gas-phase feedstock over a metal catalyst occurs without the presence of a reducing gas.

3. The method of claim 1, wherein the feedstock is introduced continuously over the decarboxylation catalyst to continuously form ketones.

4. The method of claim 1, wherein the catalyst is a transition metal catalyst.

5. The method of claim 1 wherein the neutral support comprises a carbon support.

6. The method of claim 5 where in the carbon support comprises activated carbon.

7. The method of claim 4 wherein the transition metal is a metal selected from the metals in group VIII, group IX, group X, or group XI on the periodic table.

8. The method of claim 1 wherein the metal in the metal catalyst is a non-metal catalyst.

9. The method of claim 8 wherein the non-precious metal catalyst comprises Cu and the neutral support comprises carbon.

10. A method for generating fuels comprising the steps of:
decarboxylating a feed stock comprising levulinic acid by passing said feed stock in a gas phase over a metal catalyst on a neutral support having a pH between 5.5 and 8 at a temperature between 350-650 degrees C. to generate ketones, and
converting the ketone product over an olefin-forming catalyst to form an olefin.

11. The method of claim 10 wherein the step of decarboxylation is performed over a non-precious metal catalyst without the presence of a reducing gas.

12. The method of claim 10 wherein the feedstock is introduced continuously over the decarboxylation catalyst to continuously form ketones.

13. The method of claim 10, wherein the metal catalyst is a transition metal catalyst.

14. The method of claim 10 wherein the neutral support comprises a carbon support.

15. The method of claim 10 wherein the metal catalyst is not a precious metal.

16. The method of claim 10 wherein the transition metal is selected from the metals in group VIII, group IX, group X, or group XI on the periodic table.

17. The method of claim 1 wherein the metal catalyst comprises Cu and the neutral support comprises carbon.

18. The method of claim 10 wherein the olefin forming catalyst is a mixed-acid base catalyst.

19. The method of claim 10, wherein the olefin-forming catalyst has a formula of ZnxZryOz where x is selected from 0.5 to 15, y is selected from 0.5 to 20, and z is selected from 0.5 to 55.

* * * * *